(12) United States Patent
Blakemore et al.

(10) Patent No.: US 10,390,861 B2
(45) Date of Patent: Aug. 27, 2019

(54) SPINAL STABILIZATION DEVICE, SYSTEM, AND METHOD OF USE

(71) Applicant: K2M, Inc., Leesburg, VA (US)

(72) Inventors: Laurel Blakemore, Williston, FL (US); Robert Gaines, Columbia, MO (US); Rune Hedlund, Gothenburg (SE); Jwalant Mehta, Birmingham (GB); Kan Min, Zollikon (CH); Hilali Noordeen, London (GB); Brandon Moore, Leesburg, VA (US)

(73) Assignee: K2M, Inc., Leesburg, VA (US)

(*) Notice: Subject to any disclaimer, the term of this patent is extended or adjusted under 35 U.S.C. 154(b) by 9 days.

(21) Appl. No.: 15/660,018

(22) Filed: Jul. 26, 2017

(65) Prior Publication Data

US 2017/0333084 A1    Nov. 23, 2017

Related U.S. Application Data

(63) Continuation-in-part of application No. PCT/US2016/026379, filed on Apr. 7, 2016.
(Continued)

(51) Int. Cl.
*A61B 17/70* (2006.01)
*A61B 17/88* (2006.01)
(Continued)

(52) U.S. Cl.
CPC ...... *A61B 17/7034* (2013.01); *A61B 17/7037* (2013.01); *A61B 17/7041* (2013.01);
(Continued)

(58) Field of Classification Search
CPC ............ A61B 17/7034; A61B 17/7037; A61B 17/7041; A61B 17/7091; A61B 2017/564
(Continued)

(56) References Cited

U.S. PATENT DOCUMENTS 5,713,900 A    2/1998  Benzel et al.
6,050,997 A *  4/2000  Mullane ............. A61B 17/7035
                                                   606/250
(Continued)

OTHER PUBLICATIONS

International Search Report for PCT/US16/26379 dated Jul. 7, 2016.
(Continued)

*Primary Examiner* — Pedro Philogene
*Assistant Examiner* — David C Comstock
(74) *Attorney, Agent, or Firm* — Lerner, David, Littenberg, Krumholz & Mentlik, LLP

(57) ABSTRACT

A spinal stabilization device includes a rod receiving member, a collet, a plug, and a first bone screw. The rod receiving member defines a first throughhole, a collet recess aligned with the first throughhole, and a rod receiving slot offset from the first throughhole. The collet is insertable into the collet recess and defines an aperture, a plug recess aligned with the aperture, and a wall portion defining a rod securing slot configured to fix the spinal rod therein. The collet is transitionable between a first diameter, where the rod securement region defines a first diameter, and a second diameter, where the rod securement region defines a second diameter. The plug is insertable within the plug recess, and transitions the collet between the first and second diameters. The first bone screw includes a head portion and a threaded portion, and is insertable through the rod receiving member and the collet.

32 Claims, 13 Drawing Sheets

Related U.S. Application Data

(60) Provisional application No. 62/144,289, filed on Apr. 7, 2015.

(51) Int. Cl.
   *A61B 17/80* (2006.01)
   *A61B 17/56* (2006.01)

(52) U.S. Cl.
   CPC ........ *A61B 17/7091* (2013.01); *A61B 17/809* (2013.01); *A61B 2017/564* (2013.01)

(58) Field of Classification Search
   USPC ....... 606/264–272, 279, 305, 308, 318, 319, 606/328, 86 A
   See application file for complete search history.

(56) References Cited

U.S. PATENT DOCUMENTS

| | | | |
|---|---|---|---|
| 9,675,384 | B2 | 6/2017 | Gaines et al. |
| 2005/0070901 | A1 | 3/2005 | David |
| 2005/0228382 | A1 | 10/2005 | Richelsoph et al. |
| 2005/0251141 | A1 | 11/2005 | Frigg et al. |
| 2006/0149240 | A1* | 7/2006 | Jackson ............. A61B 17/7037 606/304 |
| 2007/0233062 | A1 | 10/2007 | Berry |
| 2008/0021454 | A1* | 1/2008 | Chao .................. A61B 17/7044 606/250 |
| 2008/0208257 | A1 | 8/2008 | Matthys |
| 2010/0094358 | A1* | 4/2010 | Moore ............... A61B 17/0642 606/319 |
| 2010/0222822 | A1 | 9/2010 | Farris et al. |
| 2010/0234902 | A1* | 9/2010 | Biedermann ...... A61B 17/7032 606/305 |
| 2010/0268279 | A1 | 10/2010 | Gabelberger et al. |
| 2010/0331897 | A1 | 12/2010 | Lindner |
| 2012/0029566 | A1* | 2/2012 | Rezach ............. A61B 17/7038 606/264 |
| 2012/0303062 | A1 | 11/2012 | Amstutz et al. |
| 2013/0072991 | A1 | 3/2013 | Rathbun |
| 2013/0338715 | A1 | 12/2013 | Daly et al. |

OTHER PUBLICATIONS

Written Opinion dated Oct. 19, 2017 issued in corresponding PCT Application No. PCT/US2016/026379.

* cited by examiner

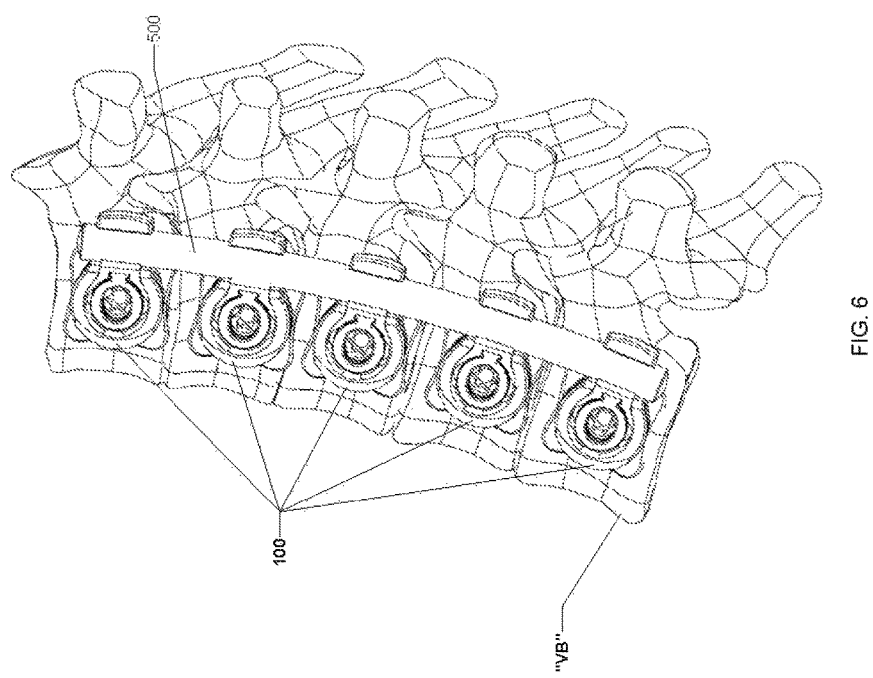

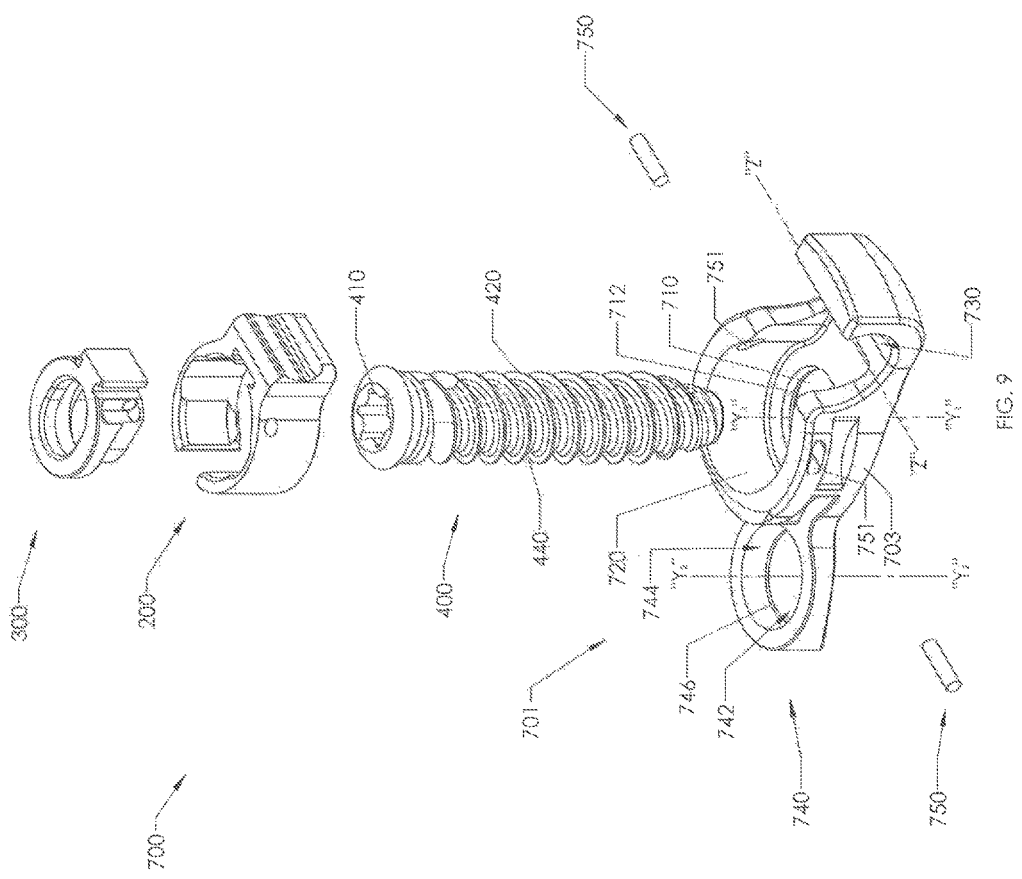

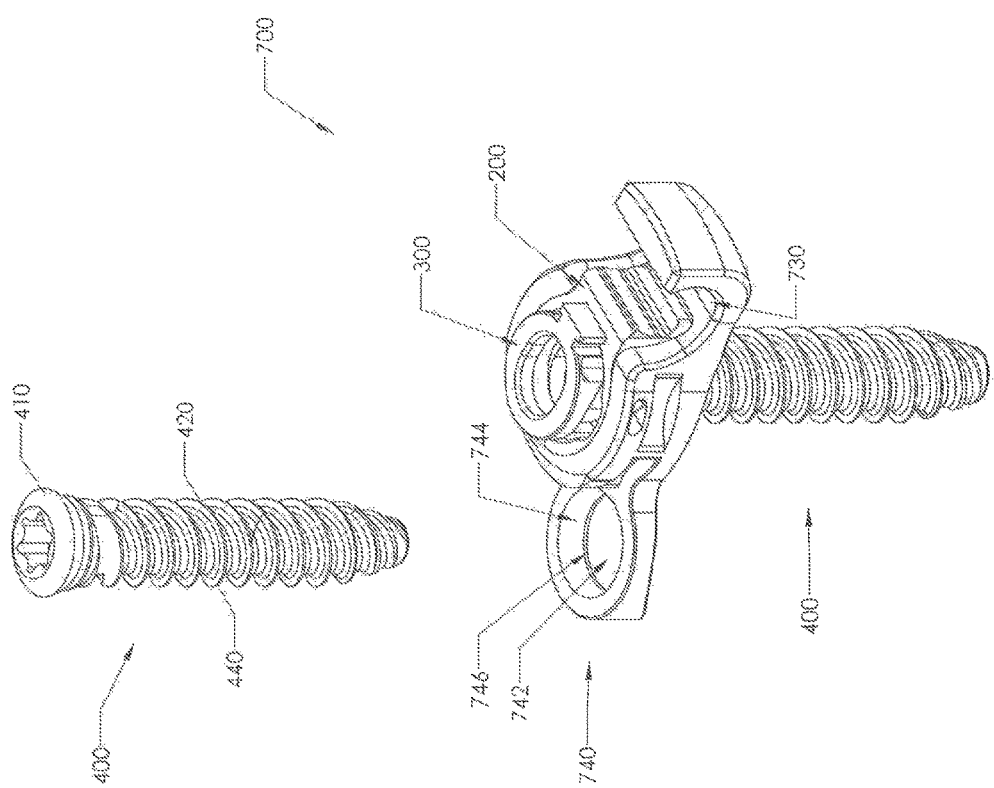

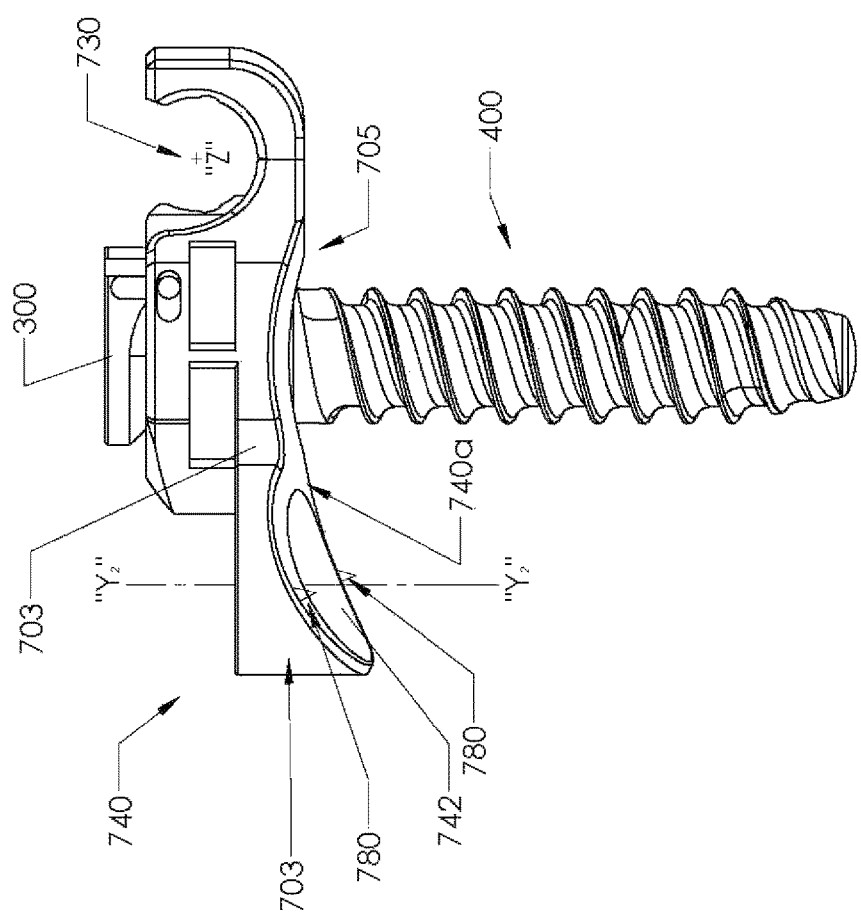

SPINAL STABILIZATION DEVICE, SYSTEM, AND METHOD OF USE

CROSS-REFERENCE TO RELATED APPLICATIONS

The present application is a continuation-in-part of International Application Serial No. PCT/US02016/026379 filed on Apr. 7, 2016, which claims the benefit of and priority to U.S. Provisional Application Ser. No. 62/144,289 filed on Apr. 7, 2015, the entire contents of each of which is incorporated by reference herein.

BACKGROUND

Technical Field

The present disclosure relates to an orthopedic surgery system for stabilizing and fixing the bones and joints of the body, and more particularly to a spinal stabilization device, system, and method of use.

Description of Related Art

The spinal column is a complex system of bones and connective tissues that provides support for the human body and protection for the spinal cord and nerves. The human spine is comprised of thirty-three vertebrae at birth and twenty-four as a mature adult. Between each pair of vertebrae is an intervertebral disc, which maintains the space between adjacent vertebrae and acts as a cushion under compressive, bending, and rotational loads and motions.

There are various disorders, diseases, and types of injury that the spinal column may experience in a lifetime. The problems may include but are not limited to scoliosis, kyphosis, excessive lordosis, spondylolisthesis, slipped or ruptured disc, degenerative disc disease, vertebral body fracture, and tumors. Persons suffering from any of the above conditions typically experience extreme or debilitating pain and often times diminished nerve function. These conditions and their treatments can be further complicated if the patient is suffering from osteoporosis or bone tissue thinning and loss of bone density. Spinal discs between the endplates of adjacent vertebrae in a spinal column of the human body provide critical support. However, due to injury, degradation, disease or the like, these discs can rupture, degenerate and/or protrude to such a degree that the intervertebral space between adjacent vertebrae collapses as the disc loses at least a part of its support function. This can cause impingement of the nerve roots and severe pain.

One of the more common solutions to any of the above-mentioned conditions involves a surgical procedure known as spinal fusion. A spinal fusion procedure involves fusing two or more vertebral bodies in order to stabilize or eliminate motion at the intervertebral disc or joint. To achieve this, natural or artificial bone, along with a spacing device, replaces either part, or the entire intervertebral disc to form a rigid column of bone, which is stabilized by implantable mechanical hardware.

The mechanical hardware used to immobilize the spinal column typically involves a series of bone screws, bone anchors, metal rods, plates, or any combination thereof. When the spine surgery is performed posteriorly, it is common practice to place bone screws/anchors sequentially into the vertebral bodies and then connect a metal rod between adjacent vertebral bodies. When the spine surgery is performed anteriorly, it is common practice to attach a thin metal plate directly to the vertebral bodies and secure it to each vertebral level using one or more bone screws.

However, as in the case of all spinal corrective surgery, a significant amount of instrumentation may still be required to perform the bone on bone technique. Therefore, a need exits for a spinal stabilization system, device, and method which provides easy and expeditious implantation, a reduction of the potential risks to the patient's long term health, provides for the required spinal support, remaining fixed during use, and maintains a low profile following implantation.

SUMMARY

The present disclosure is directed to a spinal stabilization device including a rod receiving member, a collet, a plug, and a first bone screw. The rod receiving member defines a first throughhole, a collet recess aligned with the first throughhole, and a rod receiving slot offset from the first throughhole. The collet is insertable into the collet recess of the rod receiving member. The collet defines an aperture, a plug recess aligned with the aperture, and a wall portion. The wall portion and the rod receiving slot cooperatively define a rod securement region configured to selectively fix a spinal rod therein. The collet is transitionable between a first diameter, wherein the rod securement region defines a first diameter, and a second, larger diameter, wherein the rod securement region defines a second, smaller diameter. The plug is insertable within the plug recess of the collet and configured to transition the collet between the first and second diameters. The collet is in the first diameter when the plug is removed and the collet is in the second diameter when the plug is inserted. The first bone screw includes a head portion and a threaded portion. The threaded portion is insertable through the first throughhole of the rod receiving member and the aperture of the collet.

In another aspect, an axis defined by the rod receiving slot may be transverse to an axis defined by the first throughhole.

In a further aspect, the threaded portion of the first bone screw may be configured to engage an inner surface defining the first throughhole of the rod receiving member.

In an aspect, the head portion of the first bone screw may be configured to deform an inner surface defining the first throughhole of the rod receiving member, such that the first bone screw is fixed thereto.

In yet another aspect, the collet may include a key feature and the plug may include a corresponding key feature such that the collet and the plug are thereby aligned.

In another aspect, the collet may include a retention feature disposed on an inner surface thereof. The retention feature may be configured to engage the head portion of the first bone screw and inhibit proximal translation thereof with respect to the collet.

In yet a further aspect, the first bone screw may further include a flat distal tip.

In an aspect, the collet may include a circumferential cutout along a portion thereof. The cutout may be configured to facilitate the transition between the first and second diameters.

In another aspect, the plug and the plug recess of the collet may be configured such that in the second diameter a top surface of the plug is flush with a top surface of the collet.

In a further aspect, the spinal stabilization device may further include a bone spike disposed on a distal surface of the rod receiving member and adapted to penetrate bone.

In yet another aspect, at least a portion of a distal surface of the rod receiving member may be arcuate.

In another aspect, at least one of the rod receiving member, the collet, or the plug may include at least one rounded edge.

In a further aspect, the first throughhole of the rod receiving member may define a first axis.

In yet another aspect, the rod receiving member may include a second throughhole configured to receive a second bone screw, the second throughhole may define a second axis that is offset from the first axis.

In an aspect, the second bone screw may be insertable through the second throughhole at an angle relative to the second axis.

In another aspect, the angle may be between about 1 degree and about 22.5 degrees.

In a further aspect, the rod receiving slot may define a third axis that is transverse to one of the first and second axes.

In yet another aspect, the second axis may be oriented at an angle relative to the first axis.

In another aspect, the first axis may be parallel to the second axis.

In a further aspect, a mounting ring may extend from an outer surface of the rod receiving member and may define the second throughhole.

In yet another aspect, the mounting ring may be integrally formed with the rod receiving member.

In an aspect, the mounting ring may define an inner surface and a lip extending inwardly from the inner surface, the lip may define a planar surface that extends towards a center of the second throughhole.

In another aspect, the rod receiving member may define at least one pin recess therethrough, the at least one pin recess may be configured to receive at least one pin to selectively lock the rod receiving member, the collet, and the plug into a unitary arrangement.

In another embodiment of the present disclosure, a method of stabilizing a spine includes engaging a head portion of a first bone screw with an inner surface of a first throughhole of a first rod receiving member, thereby coupling the first bone screw and the first rod receiving member. The method includes driving a threaded portion of the first bone screw into a first vertebra. The method further includes inserting a portion of a spinal rod into a first rod securement region. The first rod securement region is defined by a rod receiving slot of the first receiving member and a wall portion of a first collet. The first collet defines a first diameter and the first rod securement region defines a first diameter. The method also includes incrementally driving a first plug distally, with respect to the first collet, within a plug recess of the first collet such that the first collet transitions towards a second, larger diameter and the first rod securement region transitions towards a second, smaller diameter.

In an aspect, the method may include engaging a threaded portion of a second bone screw with an inner surface of a first throughhole of a second rod receiving member. The method may also include driving a threaded portion of the second bone screw into a second vertebra. The method may also include inserting a portion of the spinal rod into a second rod securement region defined by a rod receiving slot of the second receiving member and a wall portion of a second collet. The second collet may define a first diameter and the second rod securement region may define a first diameter. The method may further include incrementally driving a second plug distally, with respect to the second collet, within a plug recess of the second collet such that the second collet transitions towards a second, larger diameter and the second rod securement region transitions towards a second, smaller diameter.

In another aspect, incrementally driving the first plug or the second plug may further include incrementally driving the first plug or the second plug either simultaneously or sequentially.

In yet another aspect, the method may include completely driving the first plug distally such that the first collet defines the second, larger diameter and the first rod securement region defines the second, smaller diameter, such that a top surface of the first plug is flush with a top surface of the first collet.

In a further aspect, engaging the first bone screw and the first rod receiving member may further include deforming the inner surface defining the first throughhole of the first rod receiving member.

In an aspect, incrementally driving the first plug may further include mating the first plug and the first collet via a key feature defined on each of the first plug and the plug recess of the first collet.

In another aspect, the method may include inhibiting proximal translation of the first bone screw with respect to the first collet via engagement between a head portion of the first bone screw and a retention feature disposed on an inner surface of the first collet.

In yet another aspect, the method may include inserting a second bone screw through a second throughhole defined by a mounting ring of the first rod receiving member, the mounting ring extending from an outer surface of the first rod receiving member. The method may include driving a threaded portion of the second bone screw into the second vertebra.

In a further aspect, the method may include inserting the second bone screw at an angle relative to a longitudinal axis of the second throughhole.

BRIEF DESCRIPTION OF THE DRAWINGS

The above and other aspects and features of the present disclosure will become more apparent in light of the following detailed description when taken in conjunction with the accompanying drawings in which:

FIG. 6 is a top view of a construct using the spinal stabilization device of FIG. 1;

FIG. 9 is a front perspective view, with parts separated, of another embodiment of a spinal stabilization device in accordance with the present disclosure;

FIG. 10 is a front perspective view of the spinal stabilization device of FIG. 9, with parts assembled, and configured to receive a bone screw through a mounting ring thereof;

FIG. 11 is a side view of the spinal stabilization device of FIG. 9;

DETAILED DESCRIPTION OF EMBODIMENTS

Figure 1:
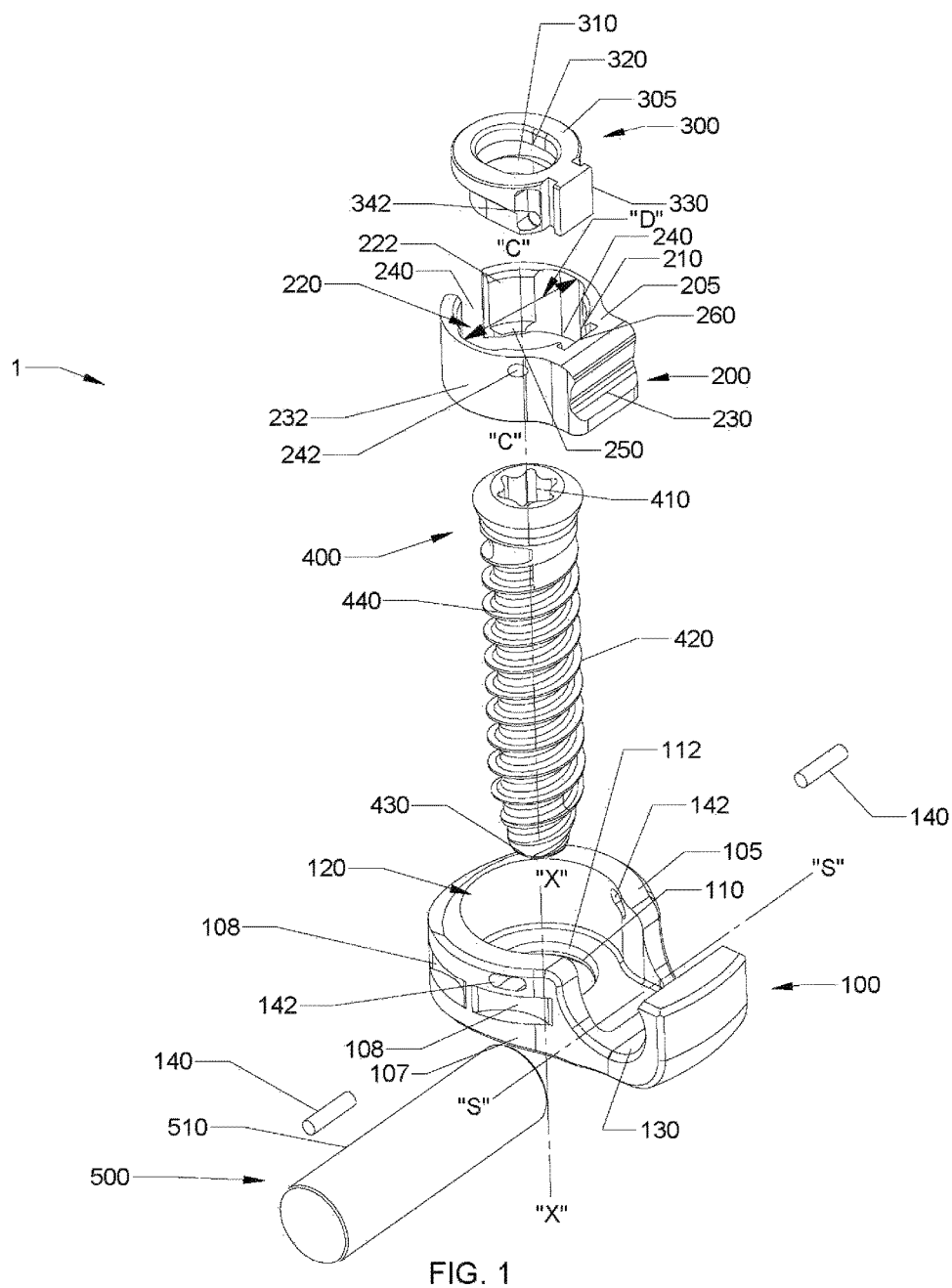
FIG. 1 is a front perspective view, with parts separated, of an embodiment of a spinal stabilization device in accordance with the present disclosure.

Embodiments of the present disclosure are now described in detail with reference to the drawings in which like reference numerals designate identical or corresponding elements in each of the several views. As is understood in the art, the term "clinician" refers to a doctor, a nurse, or any other care provider and may include support personnel. The term "proximal" refers to the portion of the apparatus or component thereof that is closer to the clinician, and the term "distal" refers to the portion of the apparatus or component thereof that is farther from the clinician.

Figure 2:
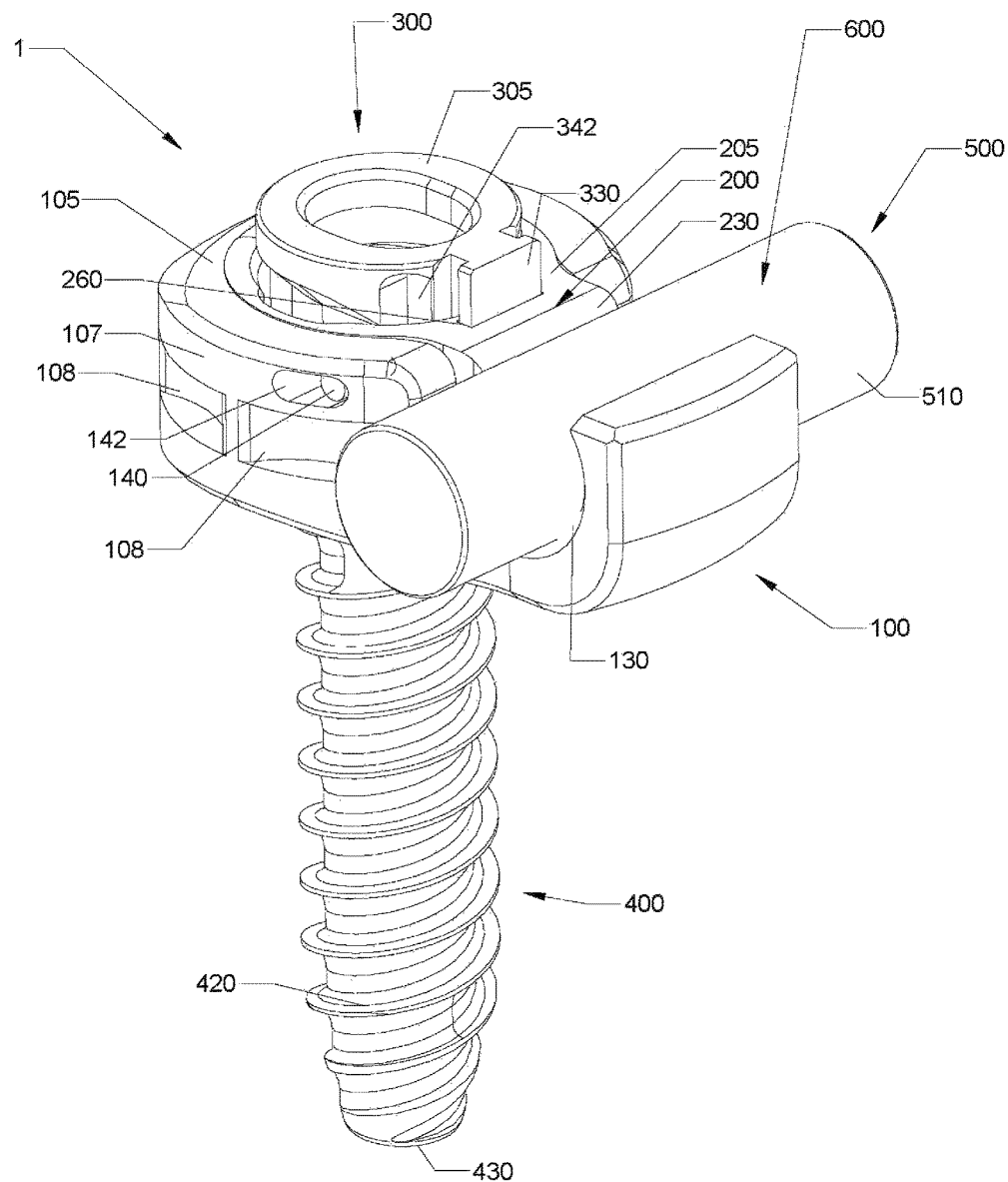
FIG. 2 is a front perspective view of the spinal stabilization device of FIG. 1, with parts assembled.
Figure 3:
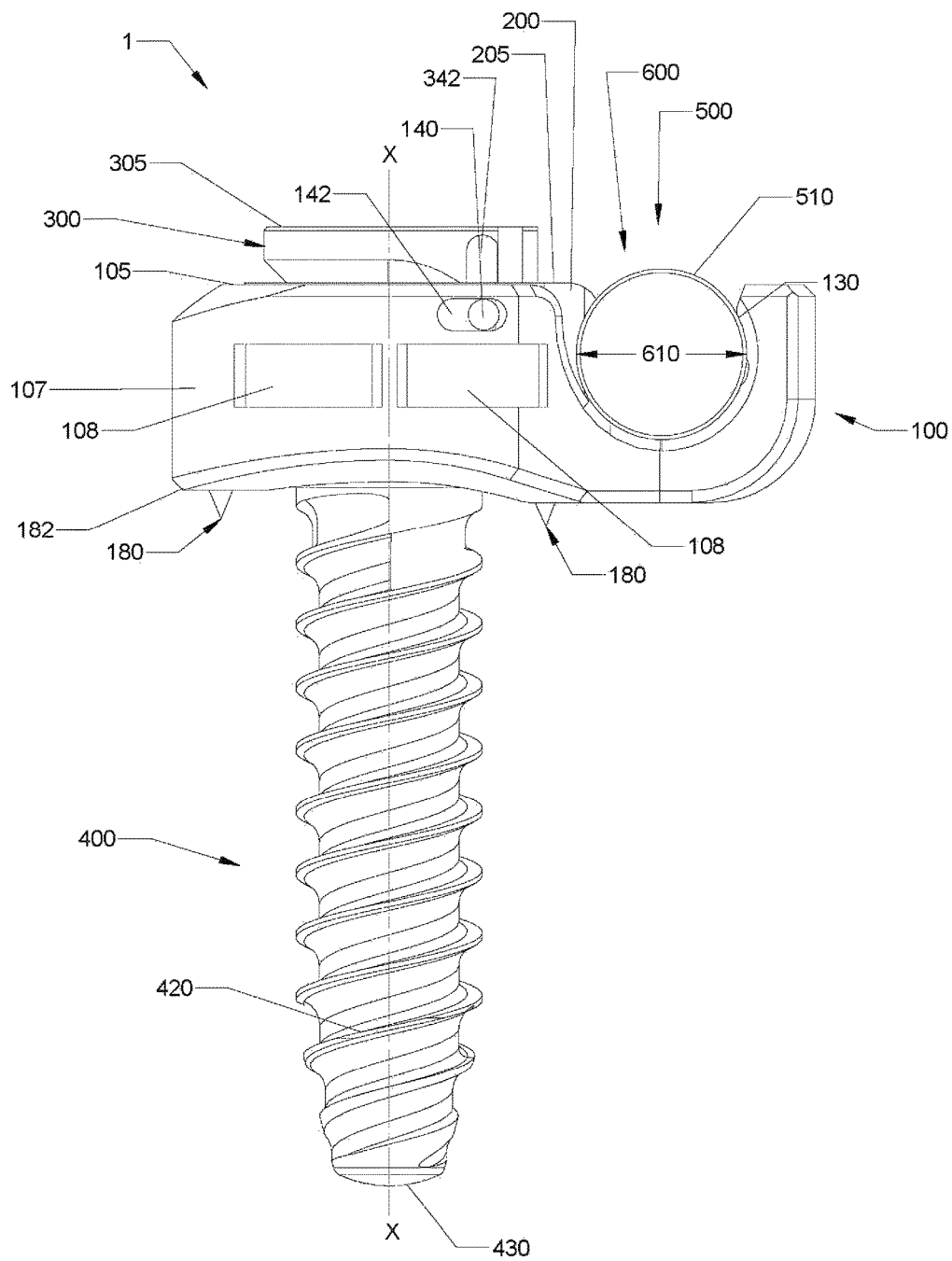
FIG. 3 is a side view of the spinal stabilization device of FIG. 2.

With reference to FIGS. 1-3, spinal stabilization device 1 includes a rod receiving member 100, a collet 200, a plug 300, and a bone screw 400. Generally, rod receiving member 100 may be secured to bone via bone screw 400. Further, spinal stabilization device 1 is transitionable between a locked configuration and an unlocked configuration, whereby a spinal rod 500 is secured to rod receiving member 100 when spinal stabilization device 1 is in the locked configuration. A spinal stabilization system 10 may include a plurality of spinal stabilization devices 1 (i.e., a plurality of rod receiving members 100, a plurality of collets 200, a plurality of plugs 300, and a plurality of bone screws 400), such that spinal stabilization system 10 forms a construct which sequentially spans across a plurality of adjacent vertebral bodies "VB" (FIG. 6). Spinal stabilization device 1 defines a low profile, of about 6 mm to about 7 mm in height extending from the normal anatomical structures fixed thereto (i.e., the combined profile of rod receiving member 100, collet 200, plug 300, and spinal rod 500, which extends away from vertebral body "VB"). The low profile of spinal stabilization device 1 allows the surgeon to easily close the surgical site, reducing pain to the patient, or minimizing irritation and damage to the surround tissue, muscle, and organs. Additionally, at least one of rod receiving member 100, collet 200, plug 300, bone screw 400, or spinal rod 500, may define at least one smooth or rounded edge and/or corner to further facilitate the surgeon's ability to close the surgical site, while reducing post-operative pain, irritation, or damage to the patient and the surround tissue, muscle, and organs.

Rod receiving member 100 defines a throughhole 110, a collet recess 120 aligned and in communication with throughhole 110, and a rod receiving slot 130 laterally offset from throughhole 110. Throughhole 110 is configured to receive a shank 440 of bone screw 400 therethrough, where an inner surface 112 defining throughhole 110 engages a head portion 410 of bone screw 400, as discussed below. Collet recess 120 is configured to slidably receive collet 200 therein. A longitudinal axis "S" is defined by rod receiving slot 130 and may be transverse to an axis "X" defined by throughhole 110. It should be appreciated that such a configuration promotes a low cross-sectional profile of rod receiving member 100, thus reducing the profile of spinal stabilization device 1. Further still, the unitary construction of rod receiving slot 130 and throughhole 110 of rod receiving member 100 provides for a singular and unobtrusive device having multiple functions within spinal stabilization system 10, as described below.

It is further envisioned that rod receiving member 100 may include one or more bone spikes 180 extending from a distal surface 182 thereof (FIG. 3). Additionally, distal surface 182 may further define an arcuate surface such that rod receiving member 100 may be set flush against vertebral body "VB" (FIG. 6). Bone spike 180 is adapted to penetrate the vertebral body "VB" such that rod receiving member 100 may be initially positioned and fixed with respect to the vertebral body "VB". Once rod receiving member 100 is positioned in a desired location, bone spikes 180 are driven into the vertebral body "VB", such that rod receiving member 100 will be resistant to twisting, sliding, or other movement during the construction of spinal stabilization device 10.

Collet 200 defines an aperture 210, a plug recess 220 aligned and in communication with aperture 210, and a wall portion 230 disposed on an external surface 232 with respect to plug recess 220. Plug recess 220 is configured to slidably receive plug 300, as discussed below. Aperture 210 is configured to transition between a first diameter (FIG. 4B) and a second diameter (FIG. 5B), where the second diameter is larger than the first diameter. As a result of aperture 210 transitioning between the first diameter and second diameters, wall portion 230 translates radially with respect to an axis "C" defined by aperture 210. Further, aperture 210 may be configured to be biased into one of the first or second diameters. Collet 200 may further include at least one circumferential cutout 240 along a portion thereof, which facilitates the radial expansion of collet 200 from a first diameter "D1" to a second, larger diameter "D2". Further still, collet 200 may include a retention feature 250 radially disposed along an inner surface 222 defining plug recess 220 (FIGS. 1, 4B, and 5B). Retention feature 250 is configured to inhibit proximal translation of bone screw 400, with respect to collet 200, as discussed below.

Figure 7:
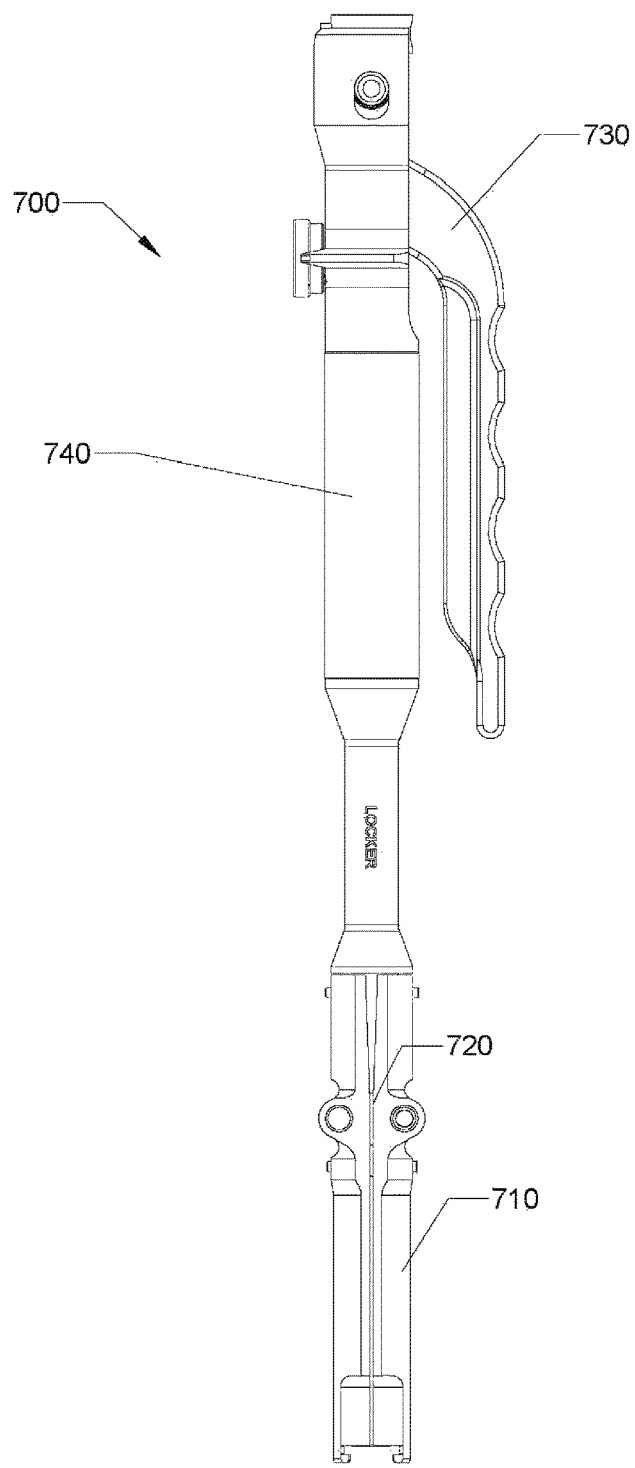
FIG. 7 is a side view of a locking instrument usable with the spinal stabilization device of FIG. 1.
Figure 8:
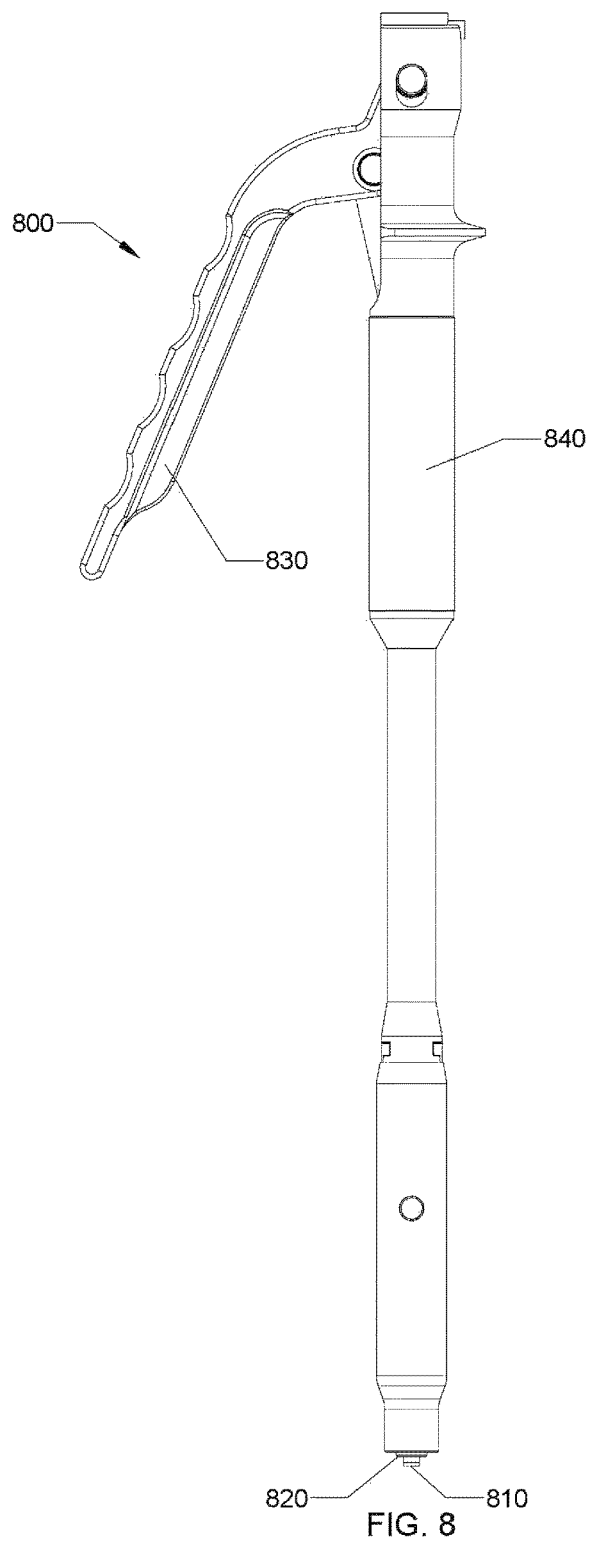
FIG. 8 is a side view of an unlocking instrument usable with the spinal stabilization device of FIG. 1.
Figure 12A:
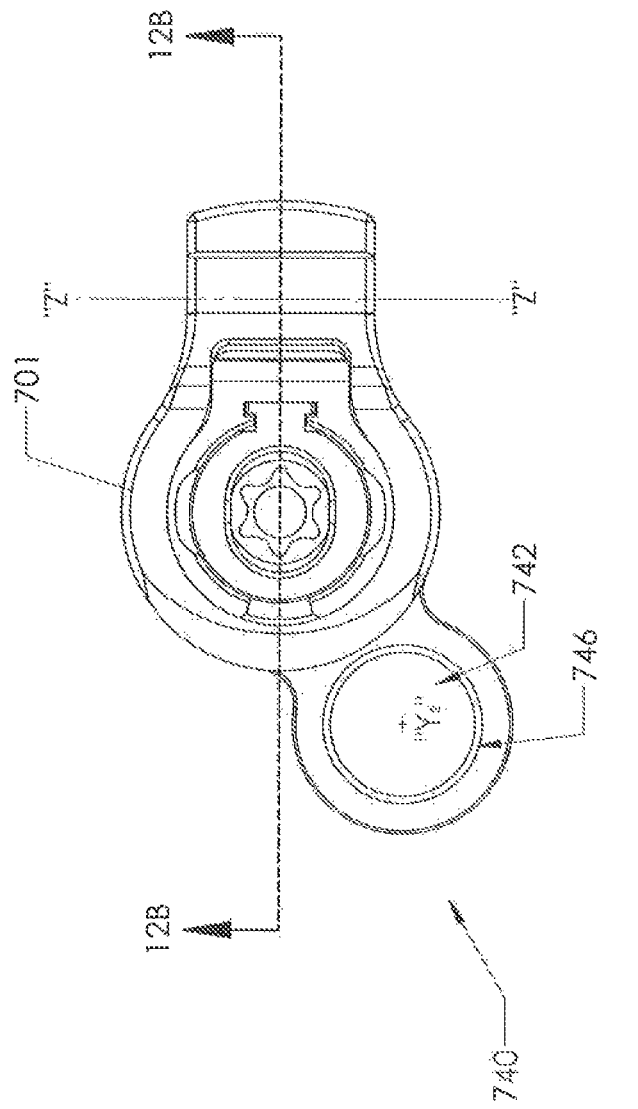
FIG. 12A is a top view of the spinal stabilization device of FIG. 11.
Figure 12B:
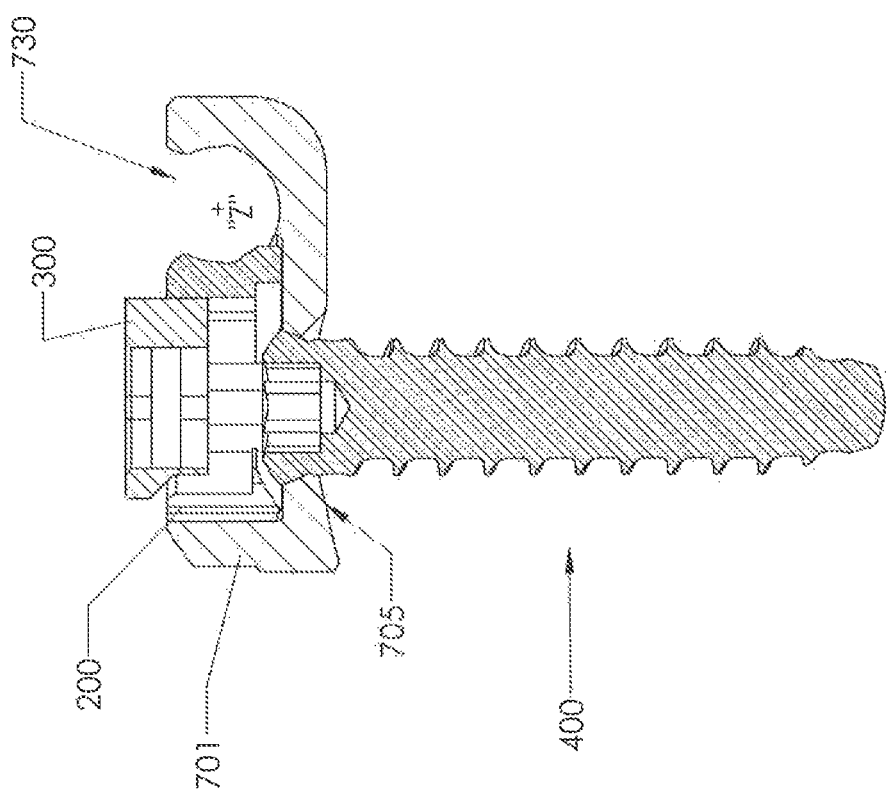
FIG. 12B is a cross-sectional view taken along section line 12B-12B of FIG. 12A.

Plug 300 defines a throughhole 310 configured to receive a drive tool (not shown) therethrough, and a head 320 configured to be engaged by a drive tool (FIGS. 7 and 8). Plug 300 is configured to be inserted into, and driven distally with respect to collet 200, via head 320. Head 320 may be configured to cooperatively engage any number of drive tools known in the art, such that a mechanical advantage is provided to effect a linear driving thereof. Plug 300 further includes a key feature 330 configured to engage a corresponding key feature 260 of collet 200, such that plug 300 may be aligned with collet 200 during insertion and distal driving thereof.

Bone screw 400 includes head portion 410 configured to mate with a drive tool (not shown), and a threaded portion 420 disposed on an outer surface of shank 440 and extending along a length thereof. Bone screw 400 is configured to be fixed to a vertebral body "VB" (FIG. 6). Head portion 410 may be configured to cooperatively engage any number of drive tools known in the art, such that torque driven rotation is effected thereof. A distal end 430 of bone screw 400 is configured such that trauma to the patient may be reduced during implantation. Distal end 430 may define a substantially flat, non-tapered, profile, a rounded or blunted profile, or an arcuate surface. Alternatively, distal end 430 may define a tapered tip with or without a cutting flute thereon.

More particularly, it is envisioned that distal end 430 may define a blunted tip having an end radius between approximately 0.125 inches to approximately 0.2 inches. Alternatively, distal end 430 may define a tapered tip of approximately 30 degrees.

As noted above, spinal rod 500 is securable to rod receiving member 100. More particularly, rod receiving slot 130 of rod receiving member 100 and wall portion 230 of collet 200 cooperatively define rod securement region 600 (FIGS. 3-5B) configured to receive and secure spinal rod 500 therein, as discussed further below. It is envisioned that spinal rod 500 may have a diameter between about 3 mm and about 8 mm. Further, that the diameter, shape, and material of spinal rod 500 may be chosen based on the requirements of the surgical procedure and the desired mechanical characteristics of spinal rod 500, e.g., rigidity, flexural modulus, flexural strength, plasticity, yield strength, etc.

Bone screw 400 is positionable within throughhole 110 of rod receiving member 100, such that a portion of threaded portion 420 of bone screw 400 engages the inner surface 112 defining throughhole 110 (FIGS. 1, 4B, and 5B). It is envisioned that head portion 410 may engage corresponding threads of inner surface 112, or may deform inner surface 112, such that bone screw 400 and rod receiving member 100 are thereby coupled. Collet 200 is insertable within collet recess 120 of rod receiving member 100, where wall portion 230 forms a portion of rod securement region 600 (FIG. 3). Further, collet 200 is configured to be completely disposed within collet recess 120, such that a top surface 205 of collet 200 may be positioned flush with a top surface 105 of rod receiving member 100, further facilitating a low profile of spinal stabilization device 1 (FIGS. 4B and 5B). In particular, top surface 105 of rod receiving member, top surface 205 of collet 200, top surface 305 of plug 300, and top surface 115 of rod receiving slot 130 are coplanar and located in plane "X" (FIG. 5B). As discussed below, collet 200 affects the diameter of rod securement region 600. Plug 300 is insertable within plug recess 220 of collet 200, and may be driven distally, with respect to collet 200, whereby key feature 320 of plug 300 cooperatively engages key feature 260 of collet 200 to facilitate insertion, alignment, and driving thereof.

At least one pin 140 couples rod receiving member 100, collet 200, and plug 300. More particularly, pin 140 is insertable within pin slot 142 of rod receiving member 100, pin hole 242 of collet 200, and pin slot 342 of plug 300. As discussed below, during distal driving of plug 300, with respect to collet 200, collet 200 transitions from the first diameter "D1" to the second diameter "D2", pin 140 slides within pin slot 142 along an axis transverse to axis "X", and slides within pin slot 342 along an axis parallel to, and laterally offset from, axis "X". It should be appreciated that during implantation, a drive tool (not shown) may pass through throughhole 310 of plug 300 and aperture 210 of collet 200, such that a portion of the drive tool may be engaged with head portion 410 of bone screw 400 to effect torque driven rotation thereof.

Figure 4A:
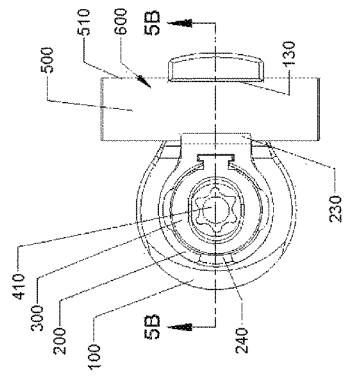
FIG. 4A is a top view of the spinal stabilization device of FIG. 2 in the unlocked configuration.
Figure 5A:
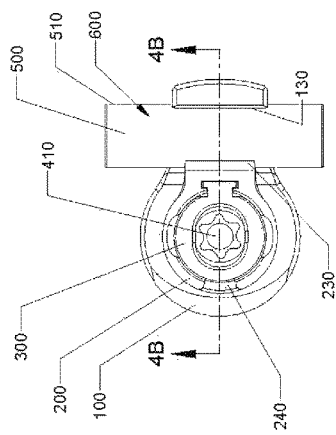
FIG. 5A is a top view of the spinal stabilization device of FIG. 2 in the locked configuration.
Figure 4B:
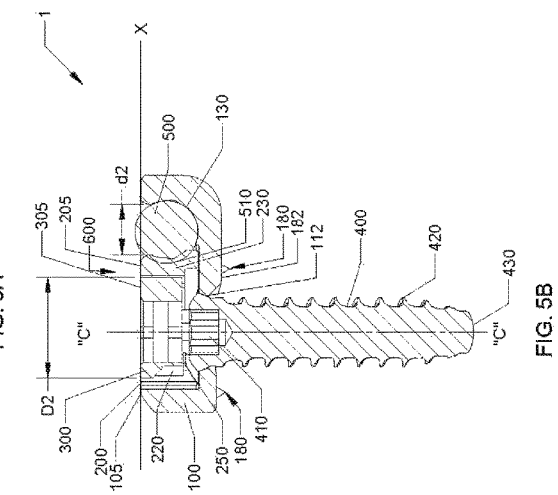
FIG. 4B is a cross-sectional view taken along section line 4B-4B of FIG. 4A.
Figure 5B:
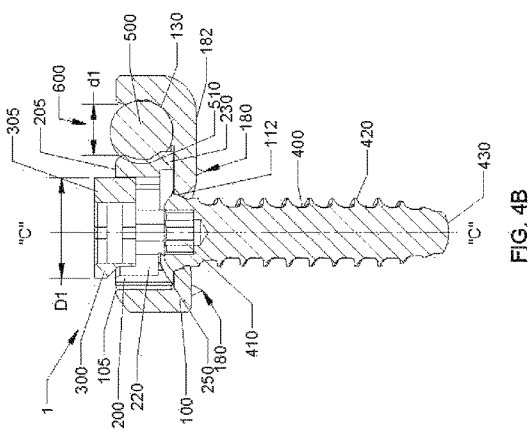
FIG. 5B is a cross-sectional view taken along section line 5B-5B of FIG. 5A.

With reference to FIGS. 4A-5B, as plug 300 is inserted into plug recess 220 of collet 200 and driven distally with respect thereto, the diameter of collet 200 transitions from the first diameter "D1" (FIGS. 4A and 4B) to the second, larger diameter "D2" (FIGS. 5A and 5B). As collet 200 transitions from the first diameter "D 1" to the second, larger diameter "D2", wall portion 230 translates radially outward, with respect to axis "C" defined by aperture 210. As wall portion 230 translates radially outward, the diameter of rod securement region 600, defined by wall portion 230 and rod receiving slot 130, transitions from a first diameter "d1" to a second, smaller diameter "d2". As should be appreciated, with spinal rod 500 disposed within rod securement region 600, and more particularly disposed between wall portion 230 and rod receiving slot 130, wall portion 230 imparts a compressive force upon an outer surface 510 of spinal rod 500. Thus, spinal rod 500 is secured within rod receiving slot 130 such that linear translation and axial rotation of spinal rod 500 with respect to rod receiving member 100 is thereby inhibited.

More particularly, with collet 200 defining the first diameter "D1", and rod securement region 600 defining the first, diameter "d1", spinal rod 500 is thereby unsecured to rod receiving member 100 and thus spinal stabilization device 1 is in the unlocked configuration (FIGS. 4A and 4B). Conversely, with collet 200 defining the second, larger diameter "D2", and rod securement region 600 defining the second, smaller diameter "d2", spinal rod 500 is thereby secured to rod receiving member 100 and thus spinal stabilization device 1 is in the locked configuration (FIGS. 5A and 5B). In the locked configuration, plug 300 is configured to be completely disposed within plug recess 220 such that a top surface 305 of plug 300 is flush with the top surface 205 of collet 200, further facilitating a low profile of spinal stabilization device 1 (FIG. 5B). As should be appreciated, in the locked configuration plug 300 and collet 200 are disposed substantially within plane "X" defined by rod receiving member 100 (FIG. 5B).

It is further envisioned that plug 300 may be incrementally driven or advanced into plug recess 220. Through incremental distal advancement of plug 300, with respect to collet 200, the diameter of collet 200 incrementally expands from the first diameter "D 1" towards the second, larger diameter "D2", such that the compressive force upon spinal rod 500 is gradually applied. As a result, spinal rod 500 may be initially or loosely secured within rod securement region 600 permitting adjustment and realignment of spinal rod 500 and spinal stabilization device 1. Plug 300 can then be completely driven and advanced distally with respect to collet 200 to fully secure spinal rod 500 within rod securement region 600.

With reference to FIGS. 1-6, in a method of stabilizing a spine using spinal stabilization device 1 a clinician may initially stretch a patient's spine by pulling on the head and feet of the patient while imaging their spine. This allows the clinician to see the segments of the spine that can easily be corrected and pin point the segments where a discectomy or spinal repair is need to be performed. This allows the clinician to operate on fewer segments of the spine and thus allow for less morbidity to the patient. It is these few segments that will be mated together in a bone on bone construct to allow fusion and the insertion of a plate member on one lateral side of the vertebral bodies "VB" to aid in stabilizing the spine. Generally, once the discectomies are complete a spinal stabilization construct is assembled.

The clinician is provided with rod receiving member 100, collet 200, plug 300, bone screw 400, and spinal rod 500. The clinician may be provided with rod receiving member 100, collet 200, and plug 300 with parts separated or with parts assembled, as discussed herein. At least one pin 750 is insertable through at least one pin recess 751 to couple rod receiving member 701, collet 200, and plug 300 to selectively lock rod receiving member 701, collet 200, and plug 300 into a unitary arrangement. Initially, the clinician may pre-drill a hole and/or directly implant bone screw 400 into the vertebral body "VB" by using a driving tool to secure threaded portion 420 of bone screw 400 into the vertebral body "VB". Bone screw 400 is positioned within the throughhole 310 of plug 300, the aperture 210 of collet 200, and the throughhole 110 of rod receiving member 100 and implanted into bone such that head portion 410 is disposed above, and proximal to, vertebral body "VB". The distal surface 182 of rod receiving member 100 is next positioned adjacent the vertebral body "VB". In embodiments including bone spike 180, bone spike 180 is brought in contact with vertebral body "VB" and fixed thereto. It is contemplated that a suitable driving tool (e.g., hammer, mallet, etc.) as known in the art may be used to drive the bone spikes 180 into the vertebral body "VB". Once rod receiving member 100 and bone screw 400 are fixed to the vertebral body "VB", if desired, compression may be performed at this point to obtain the bone on bone contact desired and any spaces may be packed with allograft, autograft, or any other fusion-promoting material known in the art.

Spinal rod 500 may be initially aligned and adjusted by the clinician as needed for the particular procedure. Next, spinal rod 500 is inserted into rod securement region 600. With spinal stabilization device 1 in the unlocked position, spinal rod 500 is positioned within rod securement region 600 and may be further adjusted or aligned as needed by the clinician. Though incremental distal driving and advancement of plug 300, with respect to collet 200, spinal rod 500 is gradually secured within rod securement region 600, and may be incrementally adjusted and aligned as needed by the clinician. Once final adjustments to spinal rod 500 are completed, plug 300 is driven distally and advanced fully within plug recess 220, such that top surface 305 of plug 300 is flush with top surface 205 of collet 200, thereby fully securing spinal rod 500 within rod securement region 600. It is envisioned that a variety of spinal rods 500 may be provided each having a different diameter, shape, and/or material.

In accordance with another embodiment of the present disclosure, the clinician may perform the method described above to form spinal stabilization system 10, i.e., to form a construct utilizing a plurality of spinal stabilization devices 1 (FIG. 6). The clinician is provided with a plurality of spinal stabilization devices 1, where each respective bone screw 400 is implanted sequentially into adjacent vertebral bodies "VB". With each respective spinal stabilization device 1 in the unlocked position, spinal rod 500 may be easily adjusted and aligned such that spinal rod 500 spans multiple vertebral bodies "VB". Further, individual spinal stabilization devices 1 may be incrementally locked, or incrementally locked, such that spinal rod 500 is incrementally secured into a respective spinal stabilization device 1.

Further to the methods disclosed herein, the clinician may be provided with a plurality of spinal stabilization devices 1 and spinal rods 500, whereby the spinal stabilization devices 1 and spinal rods 500 maintain a variety of dimensional measurements and material properties. More particularly, it is envisioned that a respective rod receiving member 100, a respective collet 200, a respective plug 300, a respective bone screw 400, a respective spinal rod 500, or any combination thereof, may define specific dimensional sizes or material properties, such that the clinician may select a desired spinal stabilization device 1 and an appropriate spinal rod 500 compatible for use therewith, or vice versa. For example, the clinician may choose a spinal rod 500 based on a specific predetermined length, diameter, or strength thereof for a given procedure, and subsequently choose a corresponding spinal stabilization device 1 having a corresponding rod securement region 600 for the chosen spinal rod 500.

In accordance with the present disclosure, a kit will be described with reference to FIGS. 1-6. The kit includes spinal stabilization device 1 having rod receiving member 100, collet 200, plug 300, and bone screw 400. The kit may further include spinal rod 500. Additionally, the kit may include a plurality of spinal stabilization devices 1 and/or spinal rods 500 such that spinal stabilization system 10 may be constructed. Further, the kit may include a plurality of spinal stabilization devices 1 and/or spinal rods 500, wherein a variety of diameters, shapes, and/or materials are provided.

With reference to FIGS. 1 and 7, spinal stabilization device 1 is configured to cooperatively engage a locking device 700. Locking device 700 includes at least one finger 710 configured to engage at least one recess 108 disposed on an external surface 107 of rod receiving member 100. It is envisioned that a plurality of recesses 108 may be radially disposed about axis "X" defined by throughhole 110. Locking device 700 further includes a driving pin 720 configured to engage head 320 of plug 300, and an actuatable drive mechanism 730 configured to drive pin 720 distally, with respect to a body portion 740 thereof. As should be appreciated, as drive mechanism 730 is actuated, and drive pin 720 is driven distally, plug 300 is driven distally, with respect to collet 200, thus transitioning spinal stabilization device 1 into the locked configuration.

With reference to FIGS. 1 and 8, spinal stabilization device 1 is configured to cooperatively engage an unlocking device 800. Unlocking device 800 includes a capturing element 810 disposed at a distal end of a drive pin 820. Capturing element 810 is configured to engage, and fixably secure to, head 320 of plug 300. An actuatable drive mechanism 830 is configured to pull drive pin 820 proximally, with respect to a body portion 840 thereof. As should be appreciated, as drive mechanisms 830 is actuated, and drive pin 820 is pulled proximally, plug 300 is pulled proximally, with respect to collet 200, thus transitioning spinal stabilization device 1 into the unlocked configuration.

With reference to FIGS. 9-12B, another embodiment of a spinal stabilization device is shown and generally referred to as 700. Spinal stabilization device 700 is substantially similar to spinal stabilization device 1 and will only described herein as necessary to describe the differences therebetween.

Spinal stabilization device 700 includes a rod receiving member 701, collet 200, plug 300, and at least one bone screw 400. Generally, rod receiving member 701 may be secured to vertebral body "VB" via one or more bone screws 400. Spinal stabilization device 700 is transitionable between an unlocked configuration and a locked configuration, wherein spinal rod 500 (FIG. 1) is securable thereto.

Rod receiving member 701 generally defines an outer surface 703, a distal surface 705, an aperture 710, a collet recess 720 aligned and in communication with aperture 710, a rod receiving slot 730 laterally offset from aperture 710, and a mounting ring 740 laterally offset from aperture 710 and rod receiving slot 730.

Aperture 710 defines a central axis "$Y_1$" and is configured to receive bone screw 400 therein. Aperture 710 defines an inner surface 712 configured to engage a head portion 410 of bone screw 400. Collet recess 720 is configured to slidably receive collet 200 therein. Rod receiving slot 730 defines a longitudinal axis "Z" that is transverse to central axis "Y₁" defined by aperture 710 and is configured to receive spinal rod 500 (FIG. 1).

Mounting ring 740 of rod receiving member 701 is configured to receive a bone screw 400 to provide supplemental affixation of spinal stabilization device 700 to vertebral body "VB." Mounting ring 740 defines an aperture 742 configured to receive shank 440 of bone screw 400 therein. Aperture 742 of mounting ring 740 defines a central axis "Y₂" that is offset from central axis "Y₁" of aperture 710, and transverse to longitudinal axis "Z" of rod receiving slot 730. Central axis "Y₂" of aperture 742 may be parallel to central axis "Y₁" of aperture 710. Alternatively, central axis "Y₂" of aperture 742 may be oriented at an angle relative to central axis Y₁" of aperture 710.

Aperture 742 of mounting ring 740 defines an inner surface 744 configured to engage head portion 410 of bone screw 400. Inner surface 744 of aperture 742 may define an annular lip 746 extending inwardly therefrom. Annular lip 746 defines a planar surface and is configured to engage threaded portion 420 of bone screw 400. A distal surface 740a of mounting ring 740 defines a radius of curvature configured to align with or conform to a natural arch or curve of vertebral body "VB" such that mounting ring 740 is flush against vertebral body "VB." Distal surface 740a of mounting ring 740 may include one or more bone spikes 780 extending therefrom, similar to the bone spikes 180 described above with respect to spinal stabilization device 1.

Figure 13:
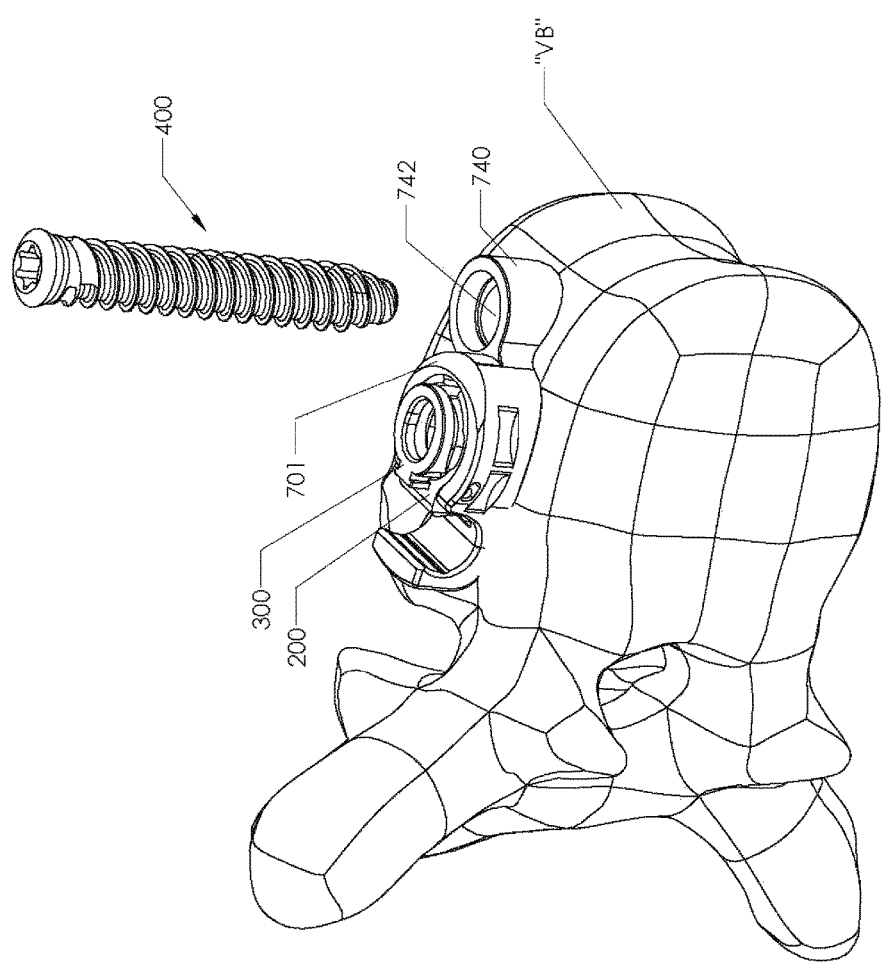
FIG. 13 is a schematic diagram showing the spinal stabilization device of FIG. 10 being secured to a vertebral body.

In use, with reference to FIG. 13, one or more spinal stabilization devices 700 is installed into vertebral bodies "VB," similar to the method described above with respect to spinal stabilization device 1. The clinician is provided with rod receiving member 701, collet 200, plug 300, bone screw 400, and spinal rod 500. Bone screw 400 is positioned within throughhole 310 of plug 300, aperture 210 of collet 200, and aperture 710 of rod receiving member 701 and implanted into vertebral body "VB," as described above with respect to spinal stabilization device 1. A second bone screw 400 can be inserted into aperture 742 of mounting ring 740 for supplemental affixation of spinal stabilization device 700 to vertebral body "VB." Specifically, distal surface 740a of mounting ring 740 is positioned adjacent to vertebral body "VB" and bone screw 400 is advanced distally into aperture 742 of mounting ring 740 and into vertebral body "VB." In embodiments, head portion 410 of bone screw 400 may deform annular lip 746 of mounting ring 740 through a reshaping process, which creates an autogenic lock to mounting ring 740 upon insertion.

In embodiments including bone spike 780, bone spike 780 is brought in contact with vertebral body "VB" and fixed thereto. Once rod receiving member 701 and bone screw 400 are fixed to the vertebral body "VB", if desired, compression may be performed to obtain the bone on bone contact desired and any spaces may be packed with allograft, autograft, or any other fusion-promoting material known in the art. Spinal rod 500 (FIG. 1) is inserted into rod receiving slot 730 and adjusted or aligned therein and secured thereto as needed.

In embodiments, mounting ring 740 may be integrally and/or monolithically formed to outer surface 703 of rod receiving member 701. Mounting ring 740 may be disposed circumferentially anywhere along outer surface 703. Rod receiving member 701 may include more than one (e.g., two, three, four, etc.) mounting rings 740 disposed circumferentially along outer surface 703.

In embodiments, bone screw 400 may be positioned within aperture 742 of mounting ring 740 with up to 15 degrees of angulation in either direction relative to central axis "Y₂" of aperture 742, providing up to 30 degrees of conical angulation. If a greater angle is required for bone screws 400, a thread former may be used, providing up to 45 degrees of angulation relative to central axis "Y₂."

In embodiments, mounting ring 740 may be bent anatomically along outer surface 703 without impairing the ability of the bone screws 400 to lock at any angle. Rod receiving member 701 may be formed from or include any biocompatible material having sufficient rigidity, such as, e.g., stainless steel, polymer, titanium or titanium alloy, ceramic, etc.

It should be appreciated that any number spinal stabilization devices 700 may be installed onto any number of vertebral bodies "VB," similar to the construct or spinal stabilization system 10 described above and shown in FIG. 6. Spinal stabilization device 700 may be used with, or without an additional bone screw 400 secured to vertebral body "VB" through mounting ring 740.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the claims of the present application and their legal equivalents, rather than by the examples given.

What is claimed is:

1. A spinal stabilization device comprising:
    a rod receiving member defining a first throughhole, a collet recess aligned with the first throughhole, and a rod receiving slot offset from the first throughhole;
    a collet insertable into the collet recess of the rod receiving member, the collet defining an aperture, a plug recess aligned with the aperture, and a wall portion, the wall portion and the rod receiving slot cooperatively defining a rod securement region configured to selectively fix a spinal rod therein, the collet transitionable between a first diameter, wherein the rod securement region defines a first diameter, and a second, larger diameter, wherein the rod securement region defines a second, smaller diameter;
    a plug insertable within the plug recess of the collet and configured to transition the collet between the first and second diameters, such that the collet is in the first diameter when the plug is removed and the collet is in the second diameter when the plug is inserted; and
    a first bone screw including a head portion and a threaded portion, the threaded portion insertable through the first throughhole of the rod receiving member and the aperture of the collet.

2. The spinal stabilization device of claim 1, wherein an axis defined by the rod receiving slot is transverse to an axis defined by the first throughhole.

3. The spinal stabilization device of claim 1, wherein the threaded portion of the first bone screw is configured to engage an inner surface defining the first throughhole of the rod receiving member.

4. The spinal stabilization device of claim 1, wherein the head portion of the first bone screw is configured to deform an inner surface defining the first throughhole of the rod receiving member, such that the first bone screw is fixed thereto.

5. The spinal stabilization device of claim 1, wherein the collet includes a key feature and the plug includes a corresponding key feature such that the collet and the plug are thereby aligned.

6. The spinal stabilization device of claim 1, wherein the collet includes a retention feature disposed on an inner surface thereof, the retention feature configured to engage the head portion of the first bone screw and inhibit proximal translation thereof with respect to the collet.

7. The spinal stabilization device of claim 1, wherein the first bone screw further includes a flat distal tip.

8. The spinal stabilization device of claim 1, wherein the collet includes a circumferential cutout along a portion thereof, the cutout configured to facilitate the transition between the first and second diameters.

9. The spinal stabilization device of claim 1, wherein the plug and the plug recess of the collet are configured such that in the second diameter a top surface of the plug is flush with a top surface of the collet.

10. The spinal stabilization device of claim 1, further including a bone spike disposed on a distal surface of the rod receiving member and adapted to penetrate bone.

11. The spinal stabilization device of claim 1, wherein at least a portion of a distal surface of the rod receiving member is arcuate.

12. The spinal stabilization device of claim 1, wherein at least one of the rod receiving member, the collet, or the plug include at least one rounded edge.

13. The spinal stabilization device of claim 1, wherein the first throughhole of the rod receiving member defines a first axis.

14. The spinal stabilization device of claim 13, wherein the rod receiving member includes a second throughhole configured to receive a second bone screw, the second throughhole defining a second axis that is offset from the first axis.

15. The spinal stabilization device of claim 14, wherein the second bone screw is insertable through the second throughhole at an angle relative to the second axis.

16. The spinal stabilization device of claim 15, wherein the angle is between about 1 degree and about 22.5 degrees.

17. The spinal stabilization device of claim 14, wherein the rod receiving slot defines a third axis that is transverse to one of the first and second axes.

18. The spinal stabilization device of claim 14, wherein the second axis is oriented at an angle relative to the first axis.

19. The spinal stabilization device of claim 14, wherein the first axis is parallel to the second axis.

20. The spinal stabilization device of claim 14, wherein a mounting ring extends from an outer surface of the rod receiving member, the mounting ring defining the second throughhole.

21. The spinal stabilization device of claim 20, wherein the mounting ring is integrally formed with the rod receiving member.

22. The spinal stabilization device of claim 20, wherein the mounting ring defines an inner surface and a lip extending inwardly from the inner surface, the lip defining a planar surface that extends towards a center of the second throughhole.

23. The spinal stabilization device of claim 1, wherein the rod receiving member defines at least one pin recess therethrough, the at least one pin recess configured to receive at least one pin to selectively lock the rod receiving member, the collet, and the plug into a unitary arrangement.

24. A stabilization method comprising:
engaging a head portion of a first bone screw with an inner surface of a first throughhole of a first rod receiving member thereby coupling the first bone screw and the first rod receiving member;
driving a threaded portion of the first bone screw into a first vertebra;
inserting a portion of a spinal rod into a first rod securement region defined by a rod receiving slot of the first receiving member and a wall portion of a first collet disposed in the first receiving member, the first collet defining a first diameter and the first rod securement region defining a first diameter; and
incrementally driving a first plug distally with respect to the first collet within a plug recess of the first collet such that the first collet transitions towards a second, larger diameter and the first rod securement region transitions towards a second, smaller diameter.

25. The method of claim 24 further including:
engaging a head portion of a second bone screw with an inner surface of a first throughhole of a second rod receiving member;
driving a threaded portion of the second bone screw into a second vertebra;
inserting a portion of the spinal rod into a second rod securement region defined by a rod receiving slot of the second receiving member and a wall portion of a second collet disposed in the second rod receiving member, the second collet defining a first diameter and the second rod securement region defining a first diameter; and
incrementally driving a second plug distally with respect to the second collet within a plug recess of the second collet such that the second collet transitions towards a second, larger diameter and the second rod securement region transitions towards a second, smaller diameter.

26. The method of claim 25, wherein incrementally driving the first plug or the second plug further includes incrementally driving the first plug or the second plug either simultaneously or sequentially.

27. The method of claim 24 further including:
completely driving the first plug distally such that the first collet defines the second, larger diameter and the first rod securement region defines the second, smaller diameter, such that a top surface of the first plug is flush with a top surface of the first collet.

28. The method of claim 24, wherein engaging the first bone screw and the first rod receiving member further includes deforming the inner surface defining the first throughhole of the first rod receiving member.

29. The method of claim 24, wherein incrementally driving the first plug further includes mating the first plug and the first collet via a key feature defined on each of the first plug and the plug recess of the first collet.

30. The method of claim 24 further including:
inhibiting proximal translation of the first bone screw with respect to the first collet via engagement between the head portion of the first bone screw and a retention feature disposed on an inner surface of the first collet.

31. The method of claim 24 further including:
inserting a second bone screw through a second throughhole defined by a mounting ring of the first rod receiving member, the mounting ring extending from an outer surface of the first rod receiving member; and
driving a threaded portion of the second bone screw into the second vertebra.

32. The method of claim 31, further including:
inserting the second bone screw at an angle relative to a longitudinal axis of the second throughhole.

* * * * *